United States Patent
Gorochow (10) Patent No.: US 11,547,414 B2
(45) Date of Patent: *Jan. 10, 2023

(54) SPIRAL DELIVERY SYSTEM FOR EMBOLIC BRAID

(71) Applicant: DePuy Synthes Products, Inc., Raynham, MA (US)

(72) Inventor: Lacey Gorochow, Raynham, MA (US)

(73) Assignee: DEPUY SYNTHES PRODUCTS, INC., Raynham, MA (US)

( * ) Notice: Subject to any disclaimer, the term of this patent is extended or adjusted under 35 U.S.C. 154(b) by 79 days.

This patent is subject to a terminal disclaimer.

(21) Appl. No.: 17/128,338

(22) Filed: Dec. 21, 2020

(65) Prior Publication Data

US 2021/0106338 A1    Apr. 15, 2021

Related U.S. Application Data

(63) Continuation of application No. 16/054,055, filed on Aug. 3, 2018, now Pat. No. 10,905,431.

(51) Int. Cl.
*A61B 17/12* (2006.01)

(52) U.S. Cl.
CPC .... *A61B 17/12113* (2013.01); *A61B 17/1214* (2013.01); *A61B 17/12031* (2013.01)

(58) Field of Classification Search
CPC ........ A61B 17/12113; A61B 17/12031; A61B 17/1214; A61B 17/12172; A61B 17/12145; A61B 17/12036; A61B 17/12168; A61B 2017/00867; A61B 2017/12054; A61B 2017/12095; A61B 17/12054; A61B 17/12095; A61B 17/1215
USPC .................................................. 606/200
See application file for complete search history.

(56) References Cited

U.S. PATENT DOCUMENTS

| | | |
|---|---|---|
| 5,861,003 A | 1/1999 | Latson et al. |
| 6,391,037 B1 | 5/2002 | Greenhalgh |
| 8,998,947 B2 | 4/2015 | Aboytes et al. |
| 9,232,992 B2 | 1/2016 | Heidner |
| 9,532,792 B2 | 1/2017 | Galdonik et al. |
| 9,532,873 B2 | 1/2017 | Kelley |
| 9,533,344 B2 | 1/2017 | Monetti et al. |
| 9,539,011 B2 | 1/2017 | Chen et al. |
| 9,539,022 B2 | 1/2017 | Bowman |
| 9,539,122 B2 | 1/2017 | Burke et al. |
| 9,539,382 B2 | 1/2017 | Nelson |
| 9,549,830 B2 | 1/2017 | Bruszewski et al. |

(Continued)

FOREIGN PATENT DOCUMENTS

WO    2008/036219 A2    3/2008

OTHER PUBLICATIONS

Extended European Search Report issued in corresponding European Patent Application No. 19 189 856 dated Dec. 3, 2019, 14 pages.

*Primary Examiner* — Robert A Lynch
(74) *Attorney, Agent, or Firm* — Troutman Pepper Hamilton Sanders LLP (57) ABSTRACT

A device for treating an aneurysm with a braided implant can include a delivery tube having a spiral groove on an outer surface of the delivery tube and a braided implant having a spiral segment. The spiral segment can engage the spiral groove as the braided implant is delivered to an aneurysm treatment site. At the treatment site, the braided implant can be implanted, and the delivery tube can be rotated to disengage the spiral segment from the spiral groove. Once released, the spiral segment can reshape to occlude the neck of the aneurysm.

17 Claims, 10 Drawing Sheets

(56) References Cited

U.S. PATENT DOCUMENTS

| | | |
|---|---|---|
| 9,554,805 B2 | 1/2017 | Tompkins et al. |
| 9,561,125 B2 | 2/2017 | Bowman et al. |
| 9,572,982 B2 | 2/2017 | Burnes et al. |
| 9,579,484 B2 | 2/2017 | Barnell |
| 9,585,642 B2 | 3/2017 | Dinsmoor et al. |
| 9,615,832 B2 | 4/2017 | Bose et al. |
| 9,615,951 B2 | 4/2017 | Bennett et al. |
| 9,622,753 B2 | 4/2017 | Cox |
| 9,636,115 B2 | 5/2017 | Henry et al. |
| 9,636,439 B2 | 5/2017 | Chu et al. |
| 9,642,675 B2 | 5/2017 | Werneth et al. |
| 9,655,633 B2 | 5/2017 | Leynov et al. |
| 9,655,645 B2 | 5/2017 | Staunton |
| 9,655,989 B2 | 5/2017 | Cruise et al. |
| 9,662,129 B2 | 5/2017 | Galdonik et al. |
| 9,662,238 B2 | 5/2017 | Dwork et al. |
| 9,662,425 B2 | 5/2017 | Lilja et al. |
| 9,668,898 B2 | 6/2017 | Wong |
| 9,675,477 B2 | 6/2017 | Thompson |
| 9,675,782 B2 | 6/2017 | Connolly |
| 9,676,022 B2 | 6/2017 | Ensign et al. |
| 9,692,557 B2 | 6/2017 | Murphy |
| 9,693,852 B2 | 7/2017 | Lam et al. |
| 9,700,262 B2 | 7/2017 | Janik et al. |
| 9,700,399 B2 | 7/2017 | Acosta-Acevedo |
| 9,717,421 B2 | 8/2017 | Griswold et al. |
| 9,717,500 B2 | 8/2017 | Tieu et al. |
| 9,717,502 B2 | 8/2017 | Teoh et al. |
| 9,724,103 B2 | 8/2017 | Cruise et al. |
| 9,724,526 B2 | 8/2017 | Strother et al. |
| 9,750,565 B2 | 9/2017 | Bloom et al. |
| 9,757,260 B2 | 9/2017 | Greenan |
| 9,764,111 B2 | 9/2017 | Gulachenski |
| 9,770,251 B2 | 9/2017 | Bowman et al. |
| 9,770,577 B2 | 9/2017 | Li et al. |
| 9,775,621 B2 | 10/2017 | Tompkins et al. |
| 9,775,706 B2 | 10/2017 | Paterson et al. |
| 9,775,732 B2 | 10/2017 | Khenansho |
| 9,788,800 B2 | 10/2017 | Mayoras, Jr. |
| 9,795,391 B2 | 10/2017 | Saatchi et al. |
| 9,801,980 B2 | 10/2017 | Karino et al. |
| 9,808,599 B2 | 11/2017 | Bowman et al. |
| 9,833,252 B2 | 12/2017 | Sepetka et al. |
| 9,833,604 B2 | 12/2017 | Lam et al. |
| 9,833,625 B2 | 12/2017 | Waldhauser et al. |
| 10,517,604 B2 | 12/2019 | Bowman et al. |
| 2003/0176909 A1 | 9/2003 | Kusleika |
| 2004/0093010 A1 | 5/2004 | Gesswein et al. |
| 2005/0187564 A1 | 8/2005 | Jayaraman |
| 2005/0288706 A1 | 12/2005 | Widomski et al. |
| 2006/0064151 A1 | 3/2006 | Guterman |
| 2007/0213813 A1 | 9/2007 | Von Segesser et al. |
| 2008/0281350 A1 | 11/2008 | Sepetka |
| 2010/0324649 A1 | 12/2010 | Mattsson |
| 2012/0283768 A1 | 11/2012 | Cox et al. |
| 2014/0135812 A1 | 5/2014 | Divino et al. |
| 2014/0200607 A1 | 7/2014 | Sepetka et al. |
| 2015/0150672 A1 | 6/2015 | Ma |
| 2017/0007264 A1 | 1/2017 | Cruise et al. |
| 2017/0007265 A1 | 1/2017 | Guo et al. |
| 2017/0020670 A1 | 1/2017 | Murray et al. |
| 2017/0020700 A1 | 1/2017 | Bienvenu et al. |
| 2017/0027640 A1 | 2/2017 | Kunis et al. |
| 2017/0027692 A1 | 2/2017 | Bonhoeffer et al. |
| 2017/0027725 A1 | 2/2017 | Argentine |
| 2017/0035436 A1 | 2/2017 | Morita |
| 2017/0035567 A1 | 2/2017 | Duffy |
| 2017/0042548 A1 | 2/2017 | Lam |
| 2017/0049596 A1 | 2/2017 | Schabert |
| 2017/0071737 A1 | 3/2017 | Kelley |
| 2017/0072452 A1 | 3/2017 | Monetti et al. |
| 2017/0079671 A1 | 3/2017 | Morero et al. |
| 2017/0079680 A1 | 3/2017 | Bowman |
| 2017/0079766 A1 | 3/2017 | Wang et al. |
| 2017/0079767 A1 | 3/2017 | Leon-Yip |
| 2017/0079812 A1 | 3/2017 | Lam et al. |
| 2017/0079817 A1 | 3/2017 | Sepetka et al. |
| 2017/0079819 A1 | 3/2017 | Pung et al. |
| 2017/0079820 A1 | 3/2017 | Lam et al. |
| 2017/0086851 A1 | 3/2017 | Wallace et al. |
| 2017/0086996 A1 | 3/2017 | Peterson et al. |
| 2017/0095259 A1 | 4/2017 | Tompkins et al. |
| 2017/0100126 A1 | 4/2017 | Bowman et al. |
| 2017/0100141 A1 | 4/2017 | Morero et al. |
| 2017/0100143 A1 | 4/2017 | Granfield |
| 2017/0100183 A1 | 4/2017 | Iaizzo et al. |
| 2017/0113023 A1 | 4/2017 | Steingisser et al. |
| 2017/0147765 A1 | 5/2017 | Mehta |
| 2017/0151032 A1 | 6/2017 | Loisel |
| 2017/0165062 A1 | 6/2017 | Rothstein |
| 2017/0165065 A1 | 6/2017 | Rothstein et al. |
| 2017/0165454 A1 | 6/2017 | Tuohy et al. |
| 2017/0172581 A1 | 6/2017 | Bose et al. |
| 2017/0172766 A1 | 6/2017 | Vong et al. |
| 2017/0172772 A1 | 6/2017 | Khenansho |
| 2017/0189033 A1 | 7/2017 | Sepetka et al. |
| 2017/0189035 A1 | 7/2017 | Porter |
| 2017/0215902 A1 | 8/2017 | Leynov et al. |
| 2017/0216484 A1 | 8/2017 | Cruise et al. |
| 2017/0224350 A1 | 8/2017 | Shimizu et al. |
| 2017/0224355 A1 | 8/2017 | Bowman et al. |
| 2017/0224467 A1 | 8/2017 | Piccagli et al. |
| 2017/0224511 A1 | 8/2017 | Dwork et al. |
| 2017/0224953 A1 | 8/2017 | Tran et al. |
| 2017/0231749 A1 | 8/2017 | Perkins et al. |
| 2017/0252064 A1 | 9/2017 | Staunton |
| 2017/0265983 A1 | 9/2017 | Lam et al. |
| 2017/0281192 A1 | 10/2017 | Tieu et al. |
| 2017/0281331 A1 | 10/2017 | Perkins et al. |
| 2017/0281344 A1 | 10/2017 | Costello |
| 2017/0281909 A1 | 10/2017 | Northrop et al. |
| 2017/0281912 A1 | 10/2017 | Melder et al. |
| 2017/0290593 A1 | 10/2017 | Cruise et al. |
| 2017/0290654 A1 | 10/2017 | Sethna |
| 2017/0296324 A1 | 10/2017 | Argentine |
| 2017/0296325 A1 | 10/2017 | Marrocco et al. |
| 2017/0303939 A1 | 10/2017 | Greenhalgh et al. |
| 2017/0303942 A1 | 10/2017 | Greenhalgh et al. |
| 2017/0303947 A1 | 10/2017 | Greenhalgh et al. |
| 2017/0303948 A1 | 10/2017 | Wallace et al. |
| 2017/0304041 A1 | 10/2017 | Argentine |
| 2017/0304097 A1 | 10/2017 | Corwin et al. |
| 2017/0304595 A1 | 10/2017 | Nagasrinivasa et al. |
| 2017/0312109 A1 | 11/2017 | Le |
| 2017/0312484 A1 | 11/2017 | Shipley et al. |
| 2017/0316561 A1 | 11/2017 | Helm et al. |
| 2017/0319826 A1 | 11/2017 | Bowman et al. |
| 2017/0333228 A1 | 11/2017 | Orth et al. |
| 2017/0333236 A1 | 11/2017 | Greenan |
| 2017/0333678 A1 | 11/2017 | Bowman et al. |
| 2017/0340383 A1 | 11/2017 | Bloom et al. |
| 2017/0348014 A1 | 12/2017 | Wallace et al. |
| 2017/0348514 A1 | 12/2017 | Guyon et al. |
| 2017/0367709 A1 | 12/2017 | Divino et al. |

FIG. 11

SPIRAL DELIVERY SYSTEM FOR EMBOLIC BRAID

CROSS REFERENCE TO RELATED APPLICATIONS

This application is a Continuation of U.S. application Ser. No. 16/054,055 filed on Aug. 3, 2018 which is incorporated herein by reference in its entirety.

FIELD OF INVENTION

This disclosure relates to medical instruments, and more particularly, delivery systems for a device for aneurysm therapy.

BACKGROUND

Cranial aneurysms can be complicated and difficult to treat due to their proximity to critical brain tissues. Prior solutions have included endovascular treatment whereby an internal volume of the aneurysm sac is removed or excluded from arterial blood pressure and flow. Current alternatives to endovascular or other surgical approaches can include occlusion devices that either fill the sac of the aneurysm with embolic material or treating the entrance or neck of the aneurysm. Both approaches attempt to prevent blood flow into the aneurysm. When filling an aneurysm sac, the embolic material clots the blood, creating a thrombotic mass within the aneurysm. When treating the aneurysm neck, blood flow into the entrance of the aneurysm is inhibited, inducing venous stasis in the aneurysm and facilitating a natural formation of a thrombotic mass within the aneurysm.

Current occlusion devices typically utilize multiple embolic coils to either fill the sac or treat the entrance. In either treatment, obtaining an embolic coil packing density sufficient to either occlude the aneurysm neck or fill the aneurysm sac is difficult and time consuming. Further, aneurysm morphology (e.g. wide neck, bifurcation, etc.) can required ancillary devices such a stents or balloons to support the coil mass and obtain the desired packing density.

Naturally formed thrombotic masses formed by treating the entrance of the aneurysm with embolic coils can improve healing compared to aneurysm masses packed with embolic coils by reducing possible distention from arterial walls and permitting reintegration into the original parent vessel shape along the neck plane. However, embolic coils delivered to the neck of the aneurysm can potentially have the adverse effect of impeding the flow of blood in the adjoining blood vessel; at the same time, if the entrance is insufficiently packed, blood flow can persist into the aneurysm. Properly implanting embolic coils is therefore challenging, and once implanted, the coils cannot easily be retracted or repositioned.

Furthermore, embolic coils do not always effectively treat aneurysms as aneurysms treated with multiple coils often recanalize or compact because of poor coiling, lack of coverage across the aneurysm neck, because of flow, or even aneurysm size.

An example alternative occlusion device is described in U.S. Pat. No. 8,998,947. However, this approach relies upon the use of embolic coils or mimics the coil approach and therefore suffers many of the limitations of embolic coil approaches such as difficulty achieving a safe packing density and inability to reposition once implanted.

It is therefore desirable to have a device which easily, accurately, and safely occludes a neck of an aneurysm or other arterio-venous malformation in a parent vessel without blocking flow into perforator vessels communicating with the parent vessel.

SUMMARY

Disclosed herein are various exemplary devices and systems of the present invention that can address the above needs. The devices generally can include a delivery tube having a spiral groove on an outer surface of the delivery tube and a braided implant having a spiral segment. The spiral segment can engage the spiral groove as the braided implant is delivered to an aneurysm treatment site. At the treatment site, the braided implant can be implanted, and the delivery tube can be rotated to disengage the spiral segment from the spiral groove. Once released, the spiral segment can reshape to occlude the neck of the aneurysm.

In one example, a system can include a delivery tube and a braided implant. The delivery tube can have a lumen, a proximal end, a distal end, and an outer surface with a spiral groove positioned near the distal end. The braided implant can have a spiral segment movable from a delivery configuration that engages the spiral groove to a deployed configuration that disengages the spiral groove. A rotation of the delivery tube in relation to the implant can move the spiral segment from the delivery configuration to the deployed configuration.

In the delivery configuration, the spiral segment and the spiral groove can each have a circular helix shape, and the spiral segment can be positioned in the spiral groove.

The braided implant can include an outer fold segment attached to the spiral segment that can be positioned over a portion of the outer surface of the delivery tube, a fold that can be positioned distal the distal end of the delivery tube, and an inner fold segment having a substantially tubular structure that can be positioned within the lumen of the delivery tube.

An inner elongated member can be positioned within the lumen of the delivery tube and can have a proximal end extending proximally from the proximal end of the delivery tube and a distal end positioned within the lumen of the delivery tube detachably attached to an end of the inner fold segment of the braided implant.

The braided implant can form an occlusive sack having an opening, and the opening can be at least partially obstructed by the spiral segment when in the deployed configuration. The opening can have a perimeter and a center. In the deployed configuration, one end of the spiral segment can attach to the occlusive sack near the perimeter while the other end can terminate near the center.

The outer fold segment and the spiral segment can each have a woven structure with a woven fiber common to both segments. Alternatively, the spiral segment can have a non-woven structure.

An example device for treating an aneurysm can include a tubular delivery member, a braided tubular implant, and a coiled element. The tubular delivery member can have a lumen, a distal end, an outer surface, and a helical structure on the outer surface. The braided tubular implant can be movable from a delivery configuration having a tubular segment extending proximally within the lumen of the tubular delivery member and an outer fold segment covering a portion of the outer surface of the delivery tube member to an implanted configuration having an occlusive sack with an opening. The coiled element can be movable from an engaging configuration that engages the helical structure on the tubular delivery member to an occluding configuration that obstructs at least a portion of the opening of the occlusive sack.

In the engaged configuration, the coiled element can have a coiled segment in the shape of a circular helix that can engage the helical structure. The helical structure can be an indentation in the shape of a circular helix.

In the occluding configuration, the coiled element can have a coiled segment in the shape of a conical helix or a planar spiral. The coiled element can have an affixed portion that can be affixed to the braided implant, and the coiled segment can have an affixed end that can be affixed to the affixed portion and a terminating end. The coiled segment can be in a shape having a first circumference measured along the coiled segment from the affixed end through one turn of the conical helix or planar spiral in the direction of the terminating end and a second circumference measured along the coiled segment from the terminating end through one turn of the conical helix or planar spiral in the direction of the affixed end such that the second circumference measures shorter than the first circumference.

The coiled element can be made of a memory shape metal, and the coiled element can move from a deformed shape in the engaging configuration to a predetermined shape in the occluding configuration.

An example method for treating an aneurysm can include the steps of providing a braided implant delivery system having a delivery tube and a braided implant, engaging a spiral segment of the braided implant with a spiral groove of the delivery tube, implanting the braided implant in the aneurysm, rotating the delivery tube in relation to the spiral segment to disengage the spiral segment from the spiral groove, and releasing the spiral segment from the delivery tube which releases the braided implant from the delivery tube.

The step of implanting the braided implant in the aneurysm can include the step of forming an occlusive sack within an aneurysm, the occlusive sack having an opening.

The method can include the step of occluding at least portion of the neck of the aneurysm with the spiral segment, and the neck can be occluded by obstructing the at least a portion of the opening of the occlusive sack.

The method can include the step of moving a portion of the spiral segment from a circular helix shape to a conical helix shape.

The method can include the steps of contacting a wall of the aneurysm with the occlusive sack, and resisting, via the contact between the aneurysm wall and the occlusive sack, a rotation of the occlusive sack in response to the rotating of the delivery tube.

The step of providing the braided implantation delivery system can include providing a delivery system that additionally includes an inner elongated member, and the method can further comprise the steps of positioning the inner elongated member in a lumen of the delivery tube and attaching the braided implant to the inner elongated member. The step of implanting the braided implant in the aneurysm can further include the steps of pushing the inner elongated member distally to invert the braided implant and form an occlusive sack within the aneurysm and detaching the braided implant from the inner elongated member.

BRIEF DESCRIPTION OF THE DRAWINGS

The above and further aspects of this invention are further discussed with reference to the following description in conjunction with the accompanying drawings, in which like numerals indicate like structural elements and features in various figures. The drawings are not necessarily to scale, emphasis instead being placed upon illustrating principles of the invention. The figures depict one or more implementations of the inventive devices, by way of example only, not by way of limitation.

DETAILED DESCRIPTION

Previous approaches utilizing embolic coils can be improved upon by treating the aneurysm entrance and/or packing the aneurysm with an embolic braided implant. For example, see U.S. patent application Ser. No. 15/903,860, incorporated herein, in its entirety, by reference. Treating the aneurysm with the braided implant can have potential advantages over treatments utilizing embolic coils such as a higher packing density, ability to retract and reposition the implant during the implantation procedure, ability to be implanted without ancillary devices such as stents or balloons, reduced risk of recanalizing or compacting, and improved coverage across the aneurysm neck, for example.

In braided implant delivery systems, it can be advantageous to maintain an attachment between the implant and the delivery system until the implant is in place at the treatment site, then detach the implant so that the delivery system can be extracted. When implanted in an aneurysm, for example, the delivery system can also serve to occlude the neck of the aneurysm. The present disclosure describes various example systems, devices, and methods that can be utilized for at least such purposes.

Figure 1A:
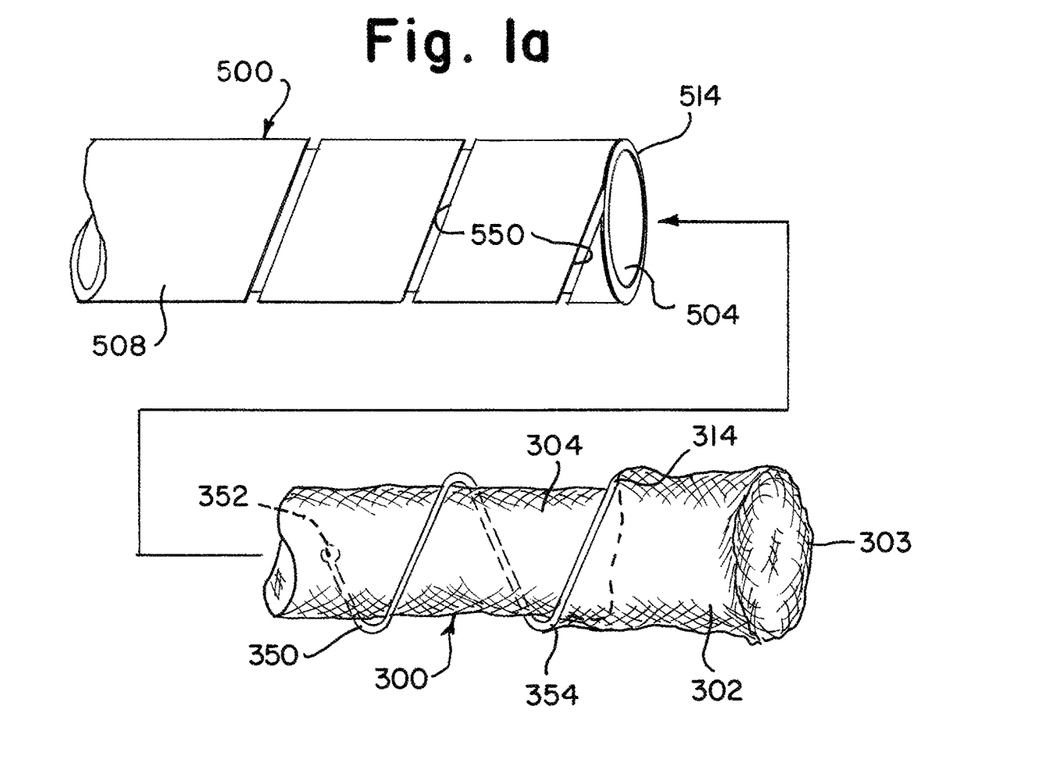
FIG. 1a illustrates an exploded view of a braided implant and a delivery tube according to the present invention.
Figure 1B:
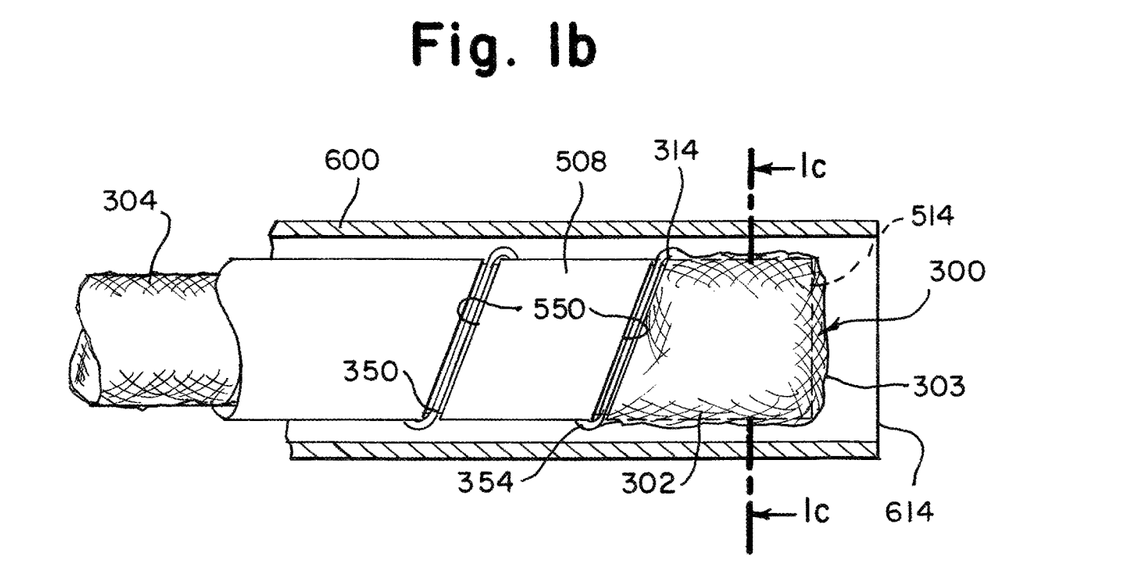
FIG. 1b illustrates a braided implant engaged with a delivery tube according to the present invention.
Figure 1C:
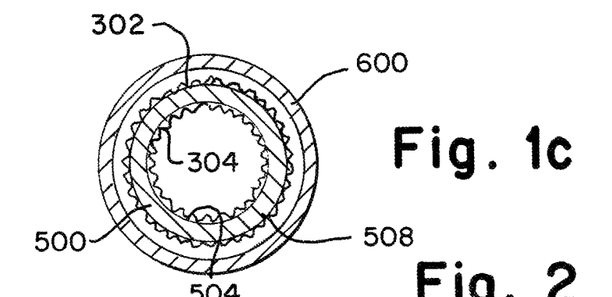
FIG. 1c illustrates a cross-sectional view of the braided implant and the delivery tube of FIG. 1b according to the present invention.

FIG. 1a illustrates an exploded view of a braided implant 300 and a delivery tube 500. The braided implant 300 is shown in a delivery configuration, shaped to be delivered to a treatment site by the delivery tube 500. FIG. 1b illustrates the braided implant 300 engaged with the delivery tube 500. The assembly illustrated in FIG. 1b is sized to be inserted into and travel through a microcatheter 600 to a treatment site. The microcatheter 600 is shown cut-away in FIG. 1b, and the delivery system is shown approaching a distal end 614 of the microcatheter 600. FIG. 1c illustrates a cross-section of the braided implant 300, delivery tube 500, and microcatheter as indicated in FIG. 1b.

Referring to FIGS. 1a to 1c collectively, the braided implant 300 can have an inner fold segment 304 shaped to be positioned within a lumen 504 of the delivery tube 500, a fold 303 that can be positioned distal a distal end 514 of the delivery tube 500, an outer fold segment 302 that can extend proximally from the fold 303 to cover a portion of an outer surface 508 of the delivery tube 500, and a spiral segment 350 that can engage a spiral groove 550 on the delivery tube 500.

The spiral segment 350 can be elongated with a helical, coiled, or spiral shape. The spiral segment 350 can have an attached end 354 attached to the outer fold segment 302 and can extend proximally to a terminating end 352. The spiral segment 350 can include a woven material with a weave that is common to the braided implant 300 such that the weave of the outer fold segment 302 and the weave of the spiral segment 350 share a common fiber. Alternatively, the spiral segment 350 can include a non-woven material and can be attached to the braided implant 300 by some other means.

The spiral segment 350 and the spiral groove 550 can be compatibly dimensioned so that the spiral segment 350 stays in place within the groove as the system is delivered through a catheter 600 to a treatment site. The groove can be deep enough for the spiral segment 350 to fit in without falling out. The width of the groove can be dimensioned to a fit such that the spiral segment 350 has minimal room to move within the groove.

Figure 2:
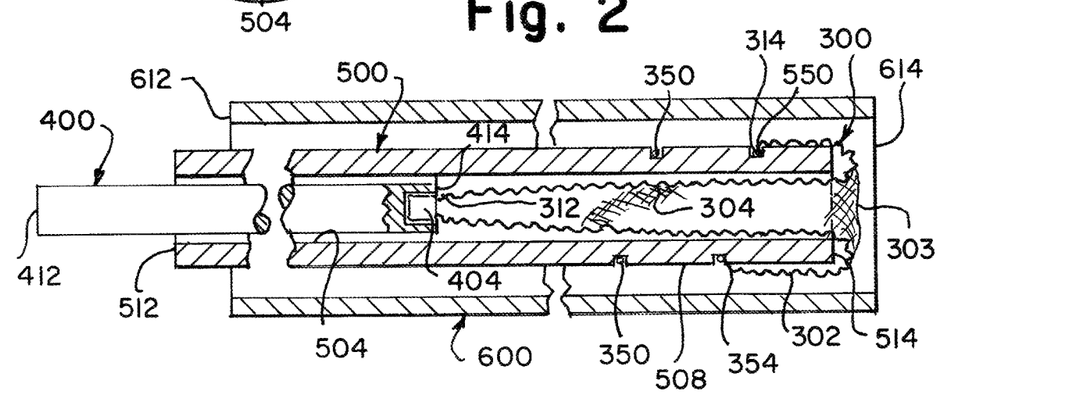
FIG. 2 illustrates a cut-sectional view delivery system according to the present invention.

FIG. 2 shows a cross-section of a delivery system including a delivery tube 500, a braided implant 300, and an inner elongated member 400. The length of the delivery system has been truncated for the purposes of the illustration.

The delivery system can be sized to be delivered to a treatment site through a catheter or microcatheter 600. The proximal end 412 of the inner elongated member 400 can extend from the proximal end 512 of the delivery tube 500, which can in turn extend from the proximal end 612 of the delivery catheter 600. The proximal end of the delivery system can be made available to a user to facilitate positioning and implantation of the braided implant 300 at a treatment site.

The braided implant 300 can include an inner fold segment 304, extending proximally during delivery and attaching at a first end 312 to the inner elongated member 400. A first end 312 of the braided implant 300 can be detachably attached to the inner elongated member 400 at a distal end 414 by a braid release 404. The inner elongated member 400 can be positioned within the lumen 504 of the delivery tube 500 having a proximal end 412 extending proximal from a proximal end 512 of the delivery tube 500.

During delivery, the inner fold segment 304 can be enveloped by the delivery tube 500 and held at the first end 312 by the inner elongated member 400. Once the delivery system is positioned at a treatment site, the inner elongated member 400 can be pushed distally, causing the inner fold segment 304 of the braided implant 300 to exit the distal end 514 of the delivery tube 500. The first end 312 of the braided implant 300 can be detached from the inner elongated member 400 at the braid release 404.

As shown in FIG. 2, the braided implant 300 can have a fold 303 distal the distal end 514 of the delivery tube 500 and an outer fold segment 302 extending proximally over an outer surface 508 of the delivery tube 500 to a second end 314 of the braided implant 300. The second end 314 of the braided implant 300 can be attached to a spiral segment 350 that can engage a spiral groove 550 in the outer surface 508 of the delivery tube 500.

Figure 3:
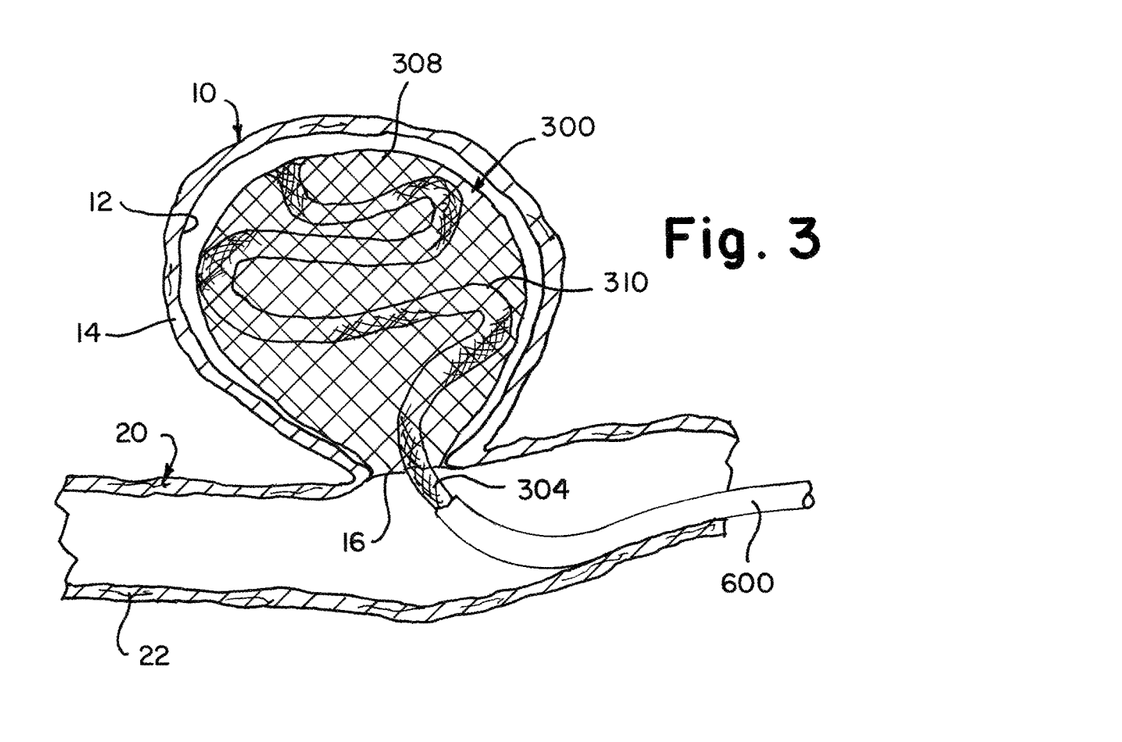
FIG. 3 illustrates a cut-away of an aneurysm during treatment according to the present invention.

FIG. 3 illustrates a cut-away of an aneurysm 10 during treatment of a delivery system including a braided implant 300. The braided implant 300 can be delivered through a blood vessel 20 to an opening 16 in the blood vessel wall 22 by a microcatheter 600. As shown, the braided implant 300 can invert to form an occlusive sack 308 that can extend to contact the aneurysm wall 14 and fill the aneurysm sac 12. Portions of the braided implant 300 not inverted can be pushed into the occlusive sack 308 by the inner elongated member 400, forming an embolic filler braid 310. FIG. 3 shows the braided implant 300 partially implanted, such that a portion of the inner fold segment 304 remains in the delivery catheter 600.

Figure 4A:
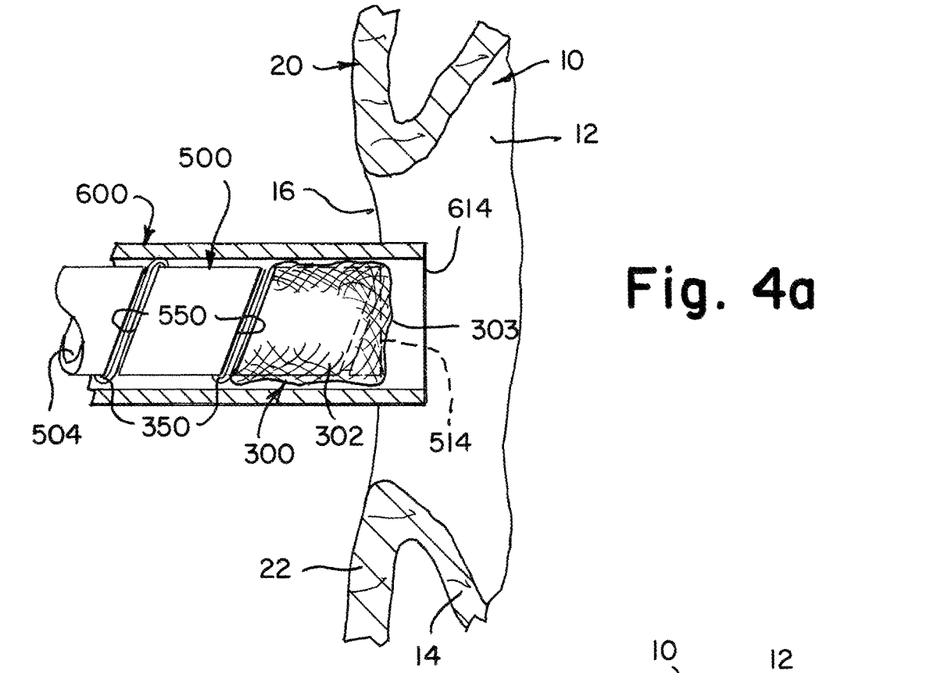
FIGS. 4a to 4e illustrate a method of use of a device of the present invention.

FIGS. 4a to 4e illustrate a method of treating an aneurysm 10 with a braided implant delivery system. FIG. 4a shows the system positioned within a blood vessel 20 at the aneurysm neck 16. FIG. 4a shows the braided implant 300 in a delivery configuration and the spiral segment 350 in an engaging configuration engaging the delivery tube 500.

Figure 4B:
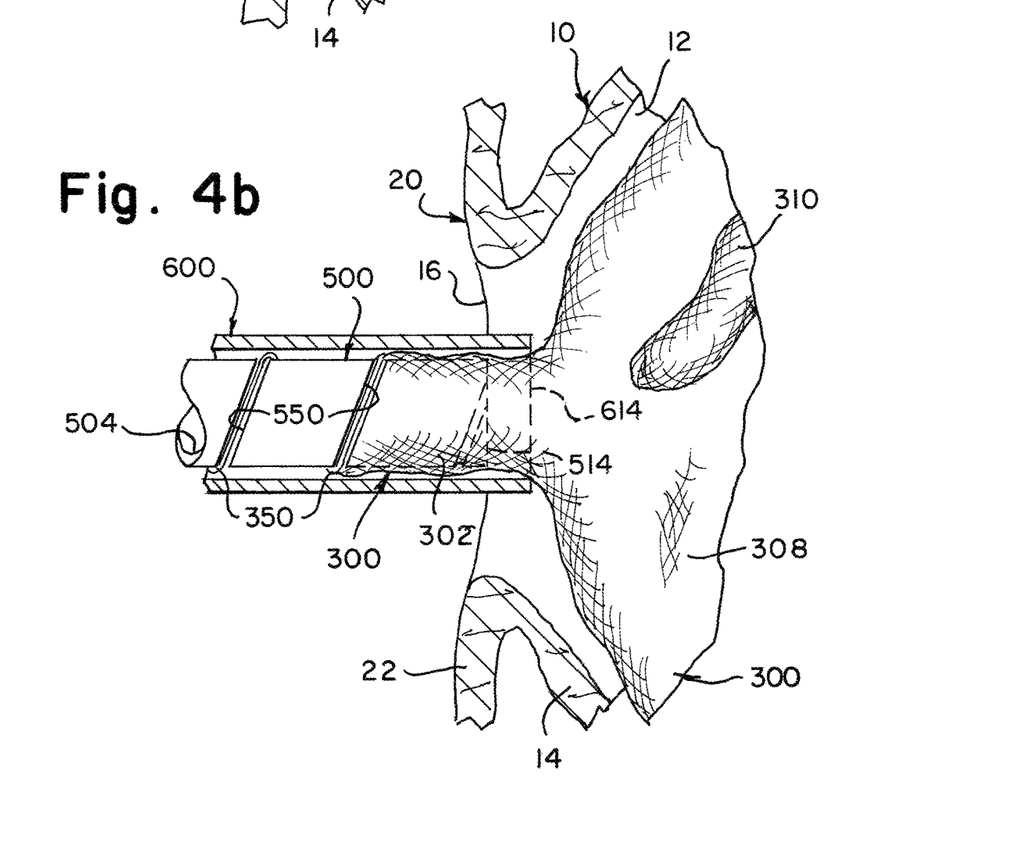

FIG. 4b shows an occlusive sack 308 and an embolic filler braid 310 that can be formed by inverting a portion of an inner fold segment 304 of the braided implant 300 and ejecting a non-inverted portion of the inner fold segment 304 respectively.

Figure 4C:
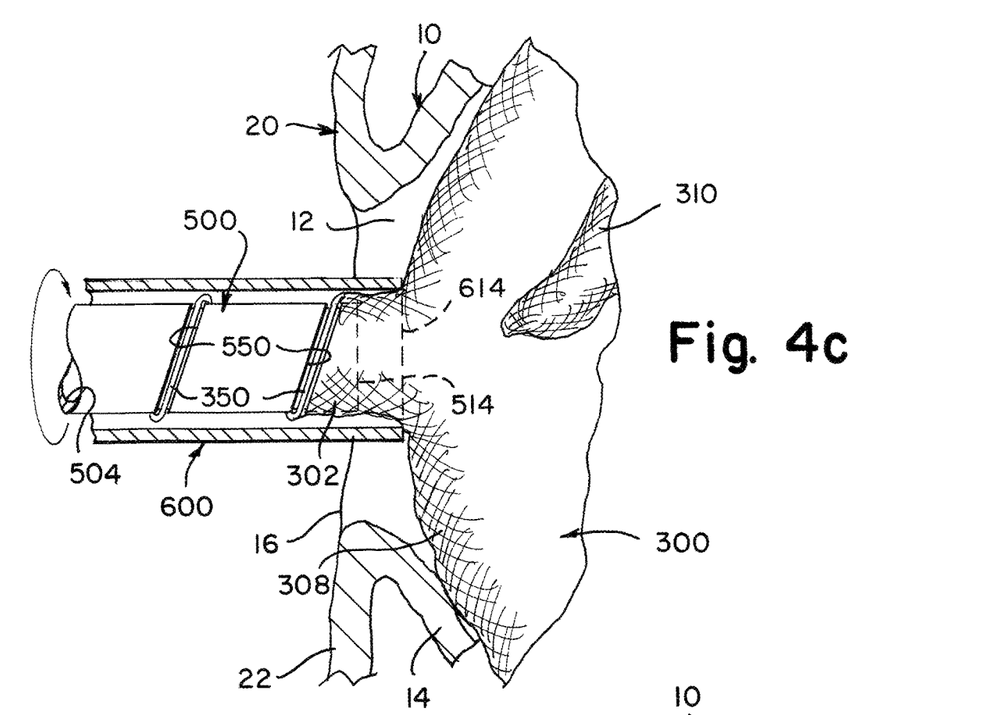

FIG. 4c shows the spiral segment 350 moving distally in response to a rotation of the delivery tube 500. The spiral segment 350 can be sized to easily glide within the spiral groove 550 as the delivery tube 500 is rotated. The occlusive sack 308 can contact the aneurysm wall 14, providing a resistance to prevent the implant 300 from rotating in response to the rotation of the delivery tube 500. As shown, the spiral segment 350 can exit the distal end 614 of the microcatheter 600 as it moves distally in response to the rotation. Alternatively (not shown), the microcatheter 600 can be retracted before rotation of the delivery tube 500.

Figure 4D:
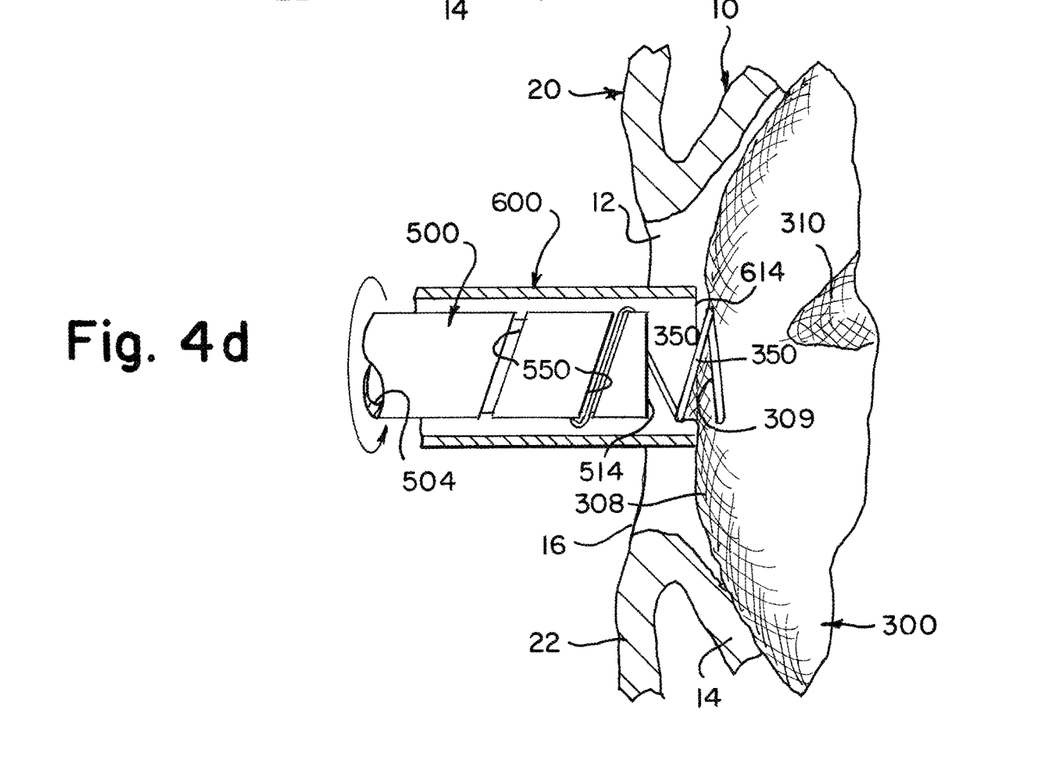

FIG. 4d shows the spiral segment 350 continuing to move distally in response to continued rotation of the delivery tube 500. As portions of the spiral segment 350 disengage the spiral groove 550, the spiral segment 350 can begin to flatten or reshape.

Figures 4E, 5:
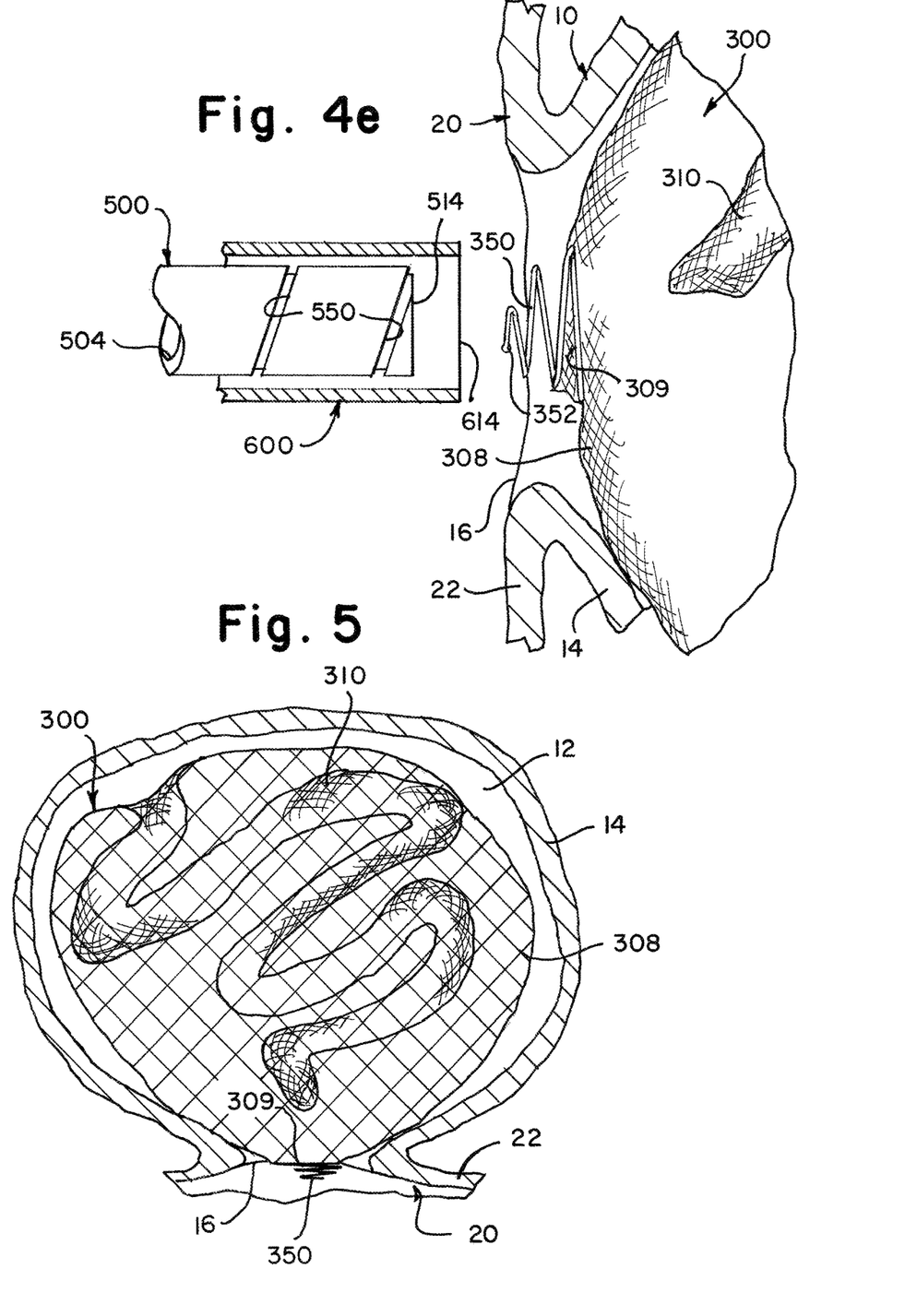
FIG. 5 illustrates a cut-away of an aneurysm implanted with a braided implant according to the present invention.

FIG. 4e shows the spiral segment 350 disengaged with the delivery tube 500 and reshaped to an occluding configuration. As shown, the spiral segment 350 can move from a circular helix shape in the engaged configuration to a conical helix shape in the occluding configuration. Alternatively, the spiral segment 350 can be otherwise shaped in either the engaging or occluding configuration as will be understood by a person of ordinary skill in the art; for example, the spiral segment 350 can occlude an aneurysm neck with a shape such as a planar spiral.

Movement of the spiral segment 350 from the engaged configuration to the occluding configuration can be accomplished by various means. For example, the spiral segment 350 can be made with a memory shape metal having a predetermined shape and a deformed shape. In such an example, the spiral segment 350 can have a deformed shape in the engaging configuration; a rotation of the delivery tube 500 can cause the spiral segment 350 to contact bodily fluid as the spiral segment 350 exits the microcatheter 600; and the spiral segment 350 can move to the predetermined shape in response to contacting the bodily fluids, the spiral segment 350 having the predetermined shape in the occluding configuration.

Alternatively, the spiral segment 350 can be made with an elastically deformable material. In such an example, the spiral segment 350 can have a stretched shape in the engaging configuration and can be sized to fit within a spiral groove 550 on an outer surface 508 of the delivery tube 500; a rotation of the delivery tube 500 can cause the spiral segment 350 to glide off of the distal end 514 of the delivery tube 500; and the spiral segment 350, now uninhibited by the delivery tube 500, can return to its original shape, the spiral segment 350 having the original shape in the occluding configuration.

FIG. 5 shows a cut-away view of an aneurysm 10 implanted with a braided implant 300. The braided implant 300 can form an occlusive sack 308 that can extend to the aneurysm wall 14, and the occlusive sack 308 can be filled with an embolic braid 310. The occlusive sack 308 and the embolic braid 310 can pack the aneurysm 10 to create a thrombotic mass, thereby providing one method of treatment to the aneurysm 10. As shown, the occlusive sack 308 can at least partially occlude the neck 16 of the aneurysm 10 reducing blood flow across the entrance to the aneurysm 10 and thereby providing a second method of treatment to the aneurysm 10. However, the occlusive sack 308 can have an opening 309 positioned in the aneurysm neck 16. Blood flow across the entrance of the aneurysm 10 can be further inhibited by obstructing the opening 309. As shown in FIG. 5, the spiral segment 350 can obstruct at least a portion of the opening 309, thereby occluding at least a portion of the neck 16 of the aneurysm 10.

Figure 6:
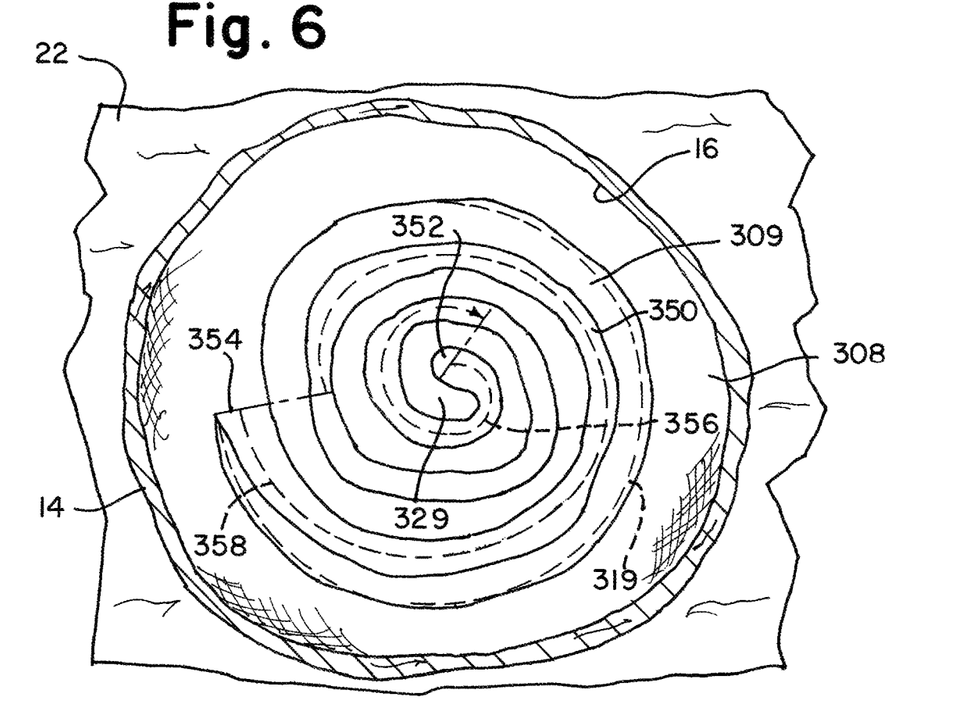
FIG. 6 illustrates a view of a braided implant as viewed at the neck of an aneurysm treated according to the present invention.

FIG. 6 depicts braided implant 300 having a spiral segment 350 implanted into an aneurysm 10 as viewed from within a blood vessel 20. From this perspective, the blood vessel wall 22 surrounds the aneurysm neck 16, and the occlusive sack 308 is shown occluding the aneurysm neck 16 around the perimeter of the aneurysm neck 16. The occlusive sack 308 is shown having an opening 309 with a perimeter 319 that is measured from the attached end 354 of the spiral segment 350, around the perimeter 319 of the opening 309 one turn. The spiral segment 350 is shown spiraling counterclockwise inward from the attached end 354 to a terminating end 352. As shown, the spiral segment 350 can have an outer circumference 358 measured starting from the attached end 354 counterclockwise in the direction of the terminating end 352 through one turn, and an inner circumference 356 measured starting from the terminating end 352 clockwise in the direction of the attached end 354 through one turn. Because the spiral segment 350 spirals inward from the attached end 354, the outer circumference 358 measures greater than the inner circumference 356. As shown, the terminating end 352 can be positioned near a center 329 of the occlusive sack opening 309.

Figure 7A:
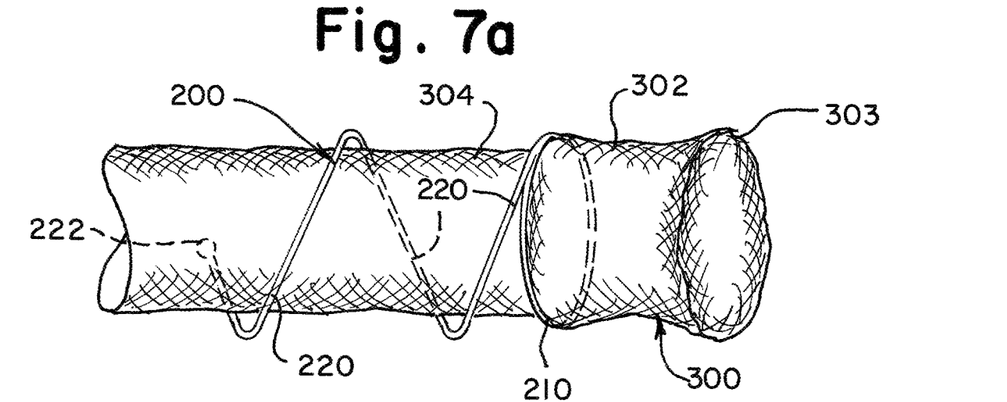
FIGS. 7a to 7b illustrate a braided implant and a coiled element according to the present invention.
Figure 7B:
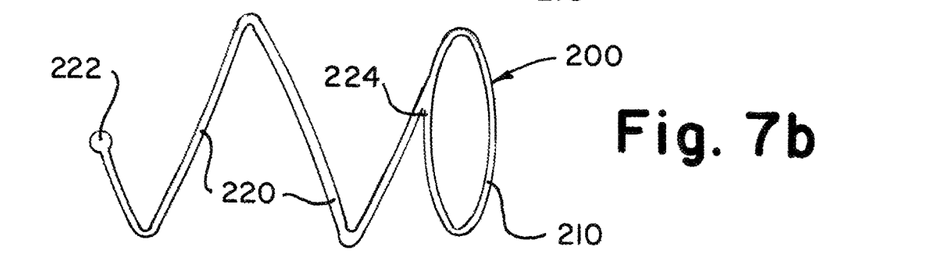

FIGS. 7a to 7b illustrate a braided implant 300 and a coiled element 200. As shown, the coiled element 200 can include an affixed portion 210 that is affixed to an end 314 of the outer fold segment 302 of the braided implant 300 and a coiled segment 220 extending from the affixed portion 210 to a terminating end 222. The affixed portion 210 can be circular, having a circumference sized to fit over an outer surface of a delivery tube (not shown), and the coiled segment 220 can have a helical shape sized to engage a helical structure on the outside of a delivery tube (not shown). FIGS. 7a and 7b show the braided implant 300 in a delivery configuration and the coiled element 200 in an engaged configuration, each configured to be delivered by a delivery tube 500 through a catheter 600 to a treatment site.

Figure 8A:
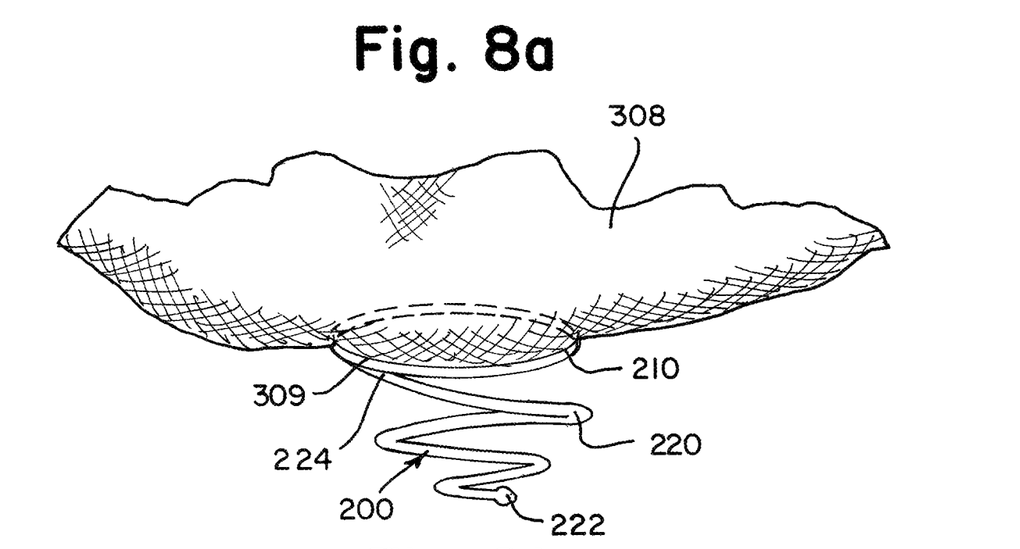
FIG. 8a illustrates a braided implant and a coiled element according to the present invention.

FIG. 8a shows a braided implant 300 in a deployed configuration and a coiled element 200 in an occluding configuration. The braided implant 300 can invert to form an occlusive sack 308, and the coiled segment 220 can move to obstruct an opening 309 in the occlusive sack 308. The occlusive sack 308 and the affixed portion 210 of the coiled element 200 can be joined at the opening 309 of the occlusive sack 308. The braided implant 300 can collapse to form a conical helix, a flattened spiral, or some other shape to obstruct the opening 309 of the occlusive sack 308.

Figure 8B:
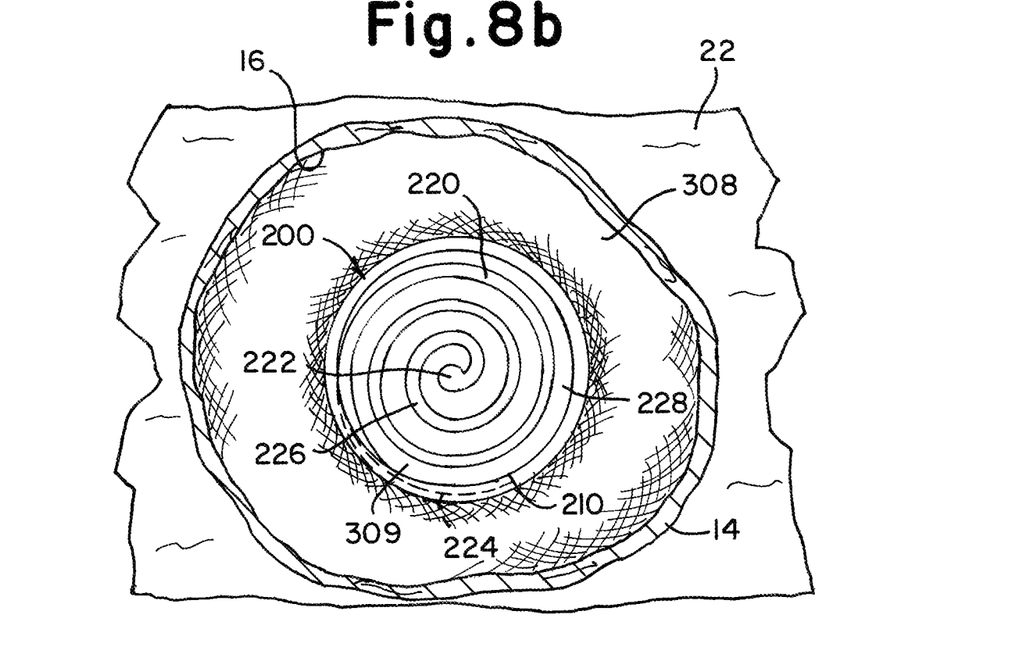
FIG. 8b illustrates a view of the braided implant and coiled element of FIG. 8a as viewed at the neck of an aneurysm treated according to the present invention.

FIG. 8b depicts a braided implant 300 and a coiled element 200 implanted into an aneurysm 10 as viewed from within a blood vessel 20. From this perspective, the blood vessel wall 22 surrounds the aneurysm neck 16. The implant 300, as shown, can include an occlusive sack 308, and the coiled element can be in an occluding configuration, for example as shown in FIG. 8a. The occlusive sack 308 can occlude a portion of the aneurysm neck 16. FIG. 8b shows the occlusive sack 308 occluding a portion of the aneurysm neck 16 around a perimeter of the aneurysm neck 16. The affixed portion 210 of the coiled element 200 can define an opening 309 of the occlusive sack 308 that is not occluded by the occlusive sack 308. The coiled element can have a coiled structure that obstructs the opening 309 of the occlusive sack 308 thereby occluding a portion of the neck 16 of the aneurysm 10.

The coiled segment 220 can rotate clockwise (as shown) or counterclockwise. The coiled segment 220 can have an outer circumference 228 measured starting at the end 224 affixed to the affixed portion 210 of the coiled element in the direction of the terminating end 222 through one turn and an inner circumference 226 measured starting at the terminating end 222 through one turn in the direction of the affixed end 224. The terminating end 222 can be positioned near the center 329 of the opening 309 of the occlusive sack 308, and the affixed end 224 can be positioned at the perimeter of the opening 309. So oriented, the outer circumference 228 can measure greater than the inner circumference 226.

Figure 9:
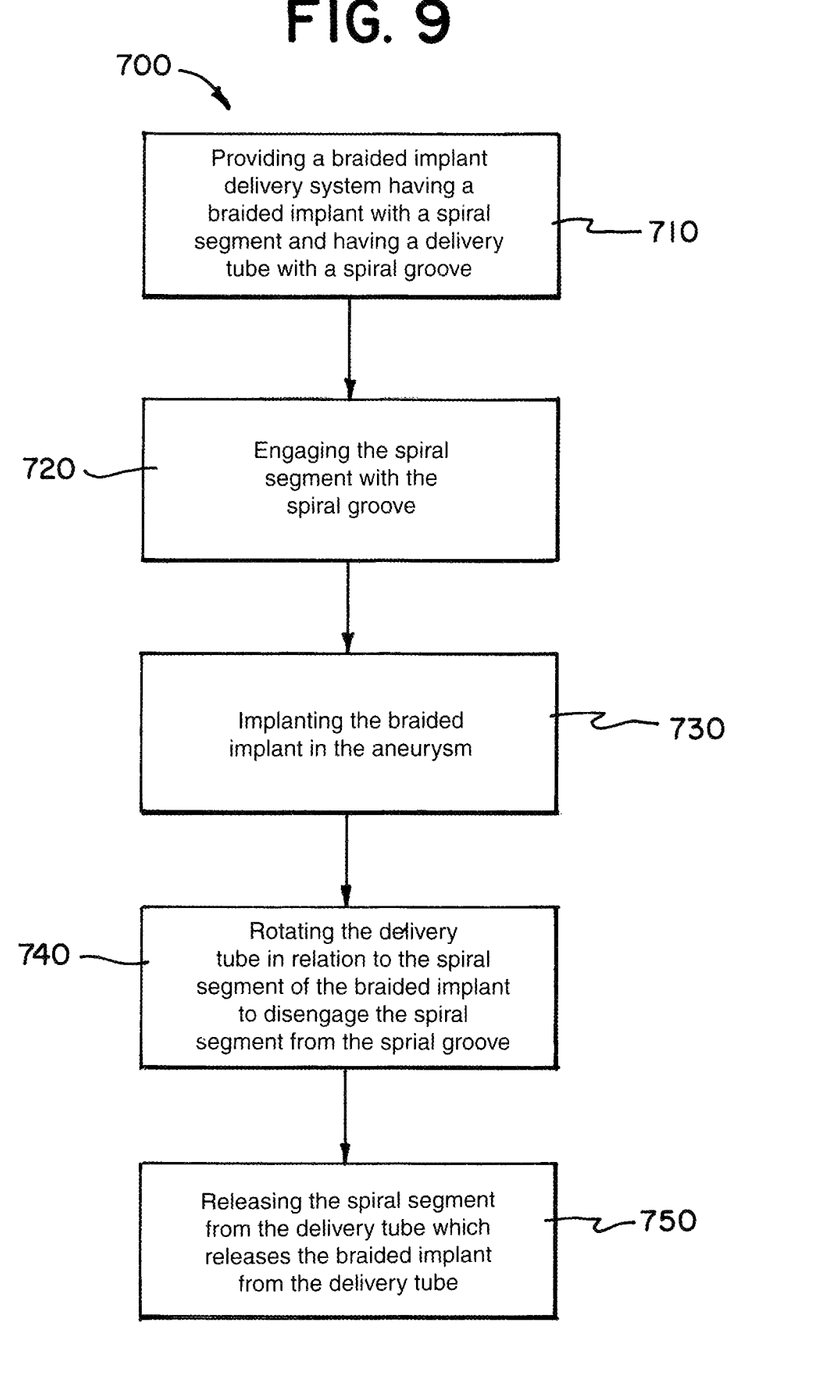
FIGS. 9 to 11 are flow diagrams outlining example method steps for use of a device according to the present invention.
Figure 10:
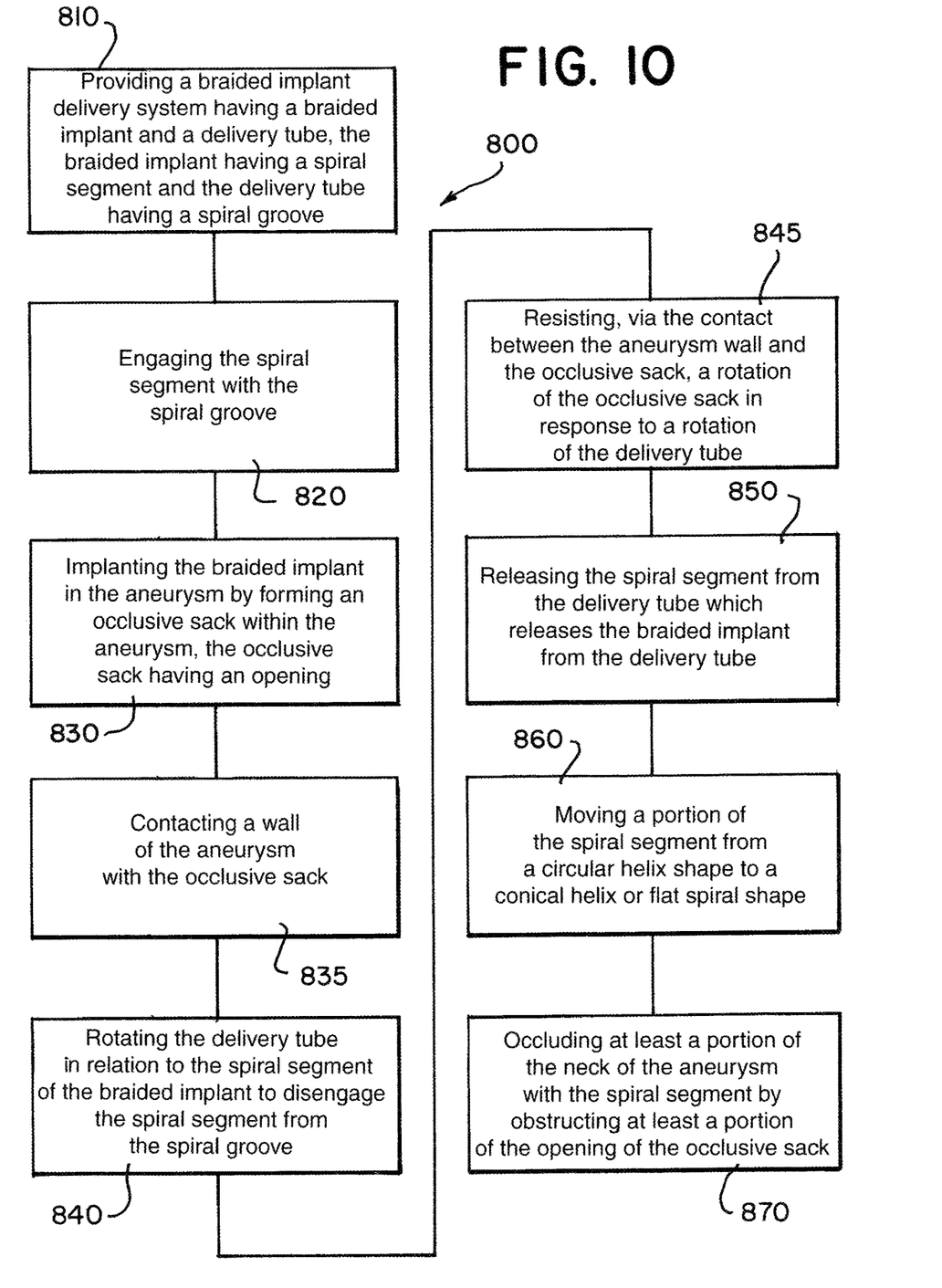
Figure 11:
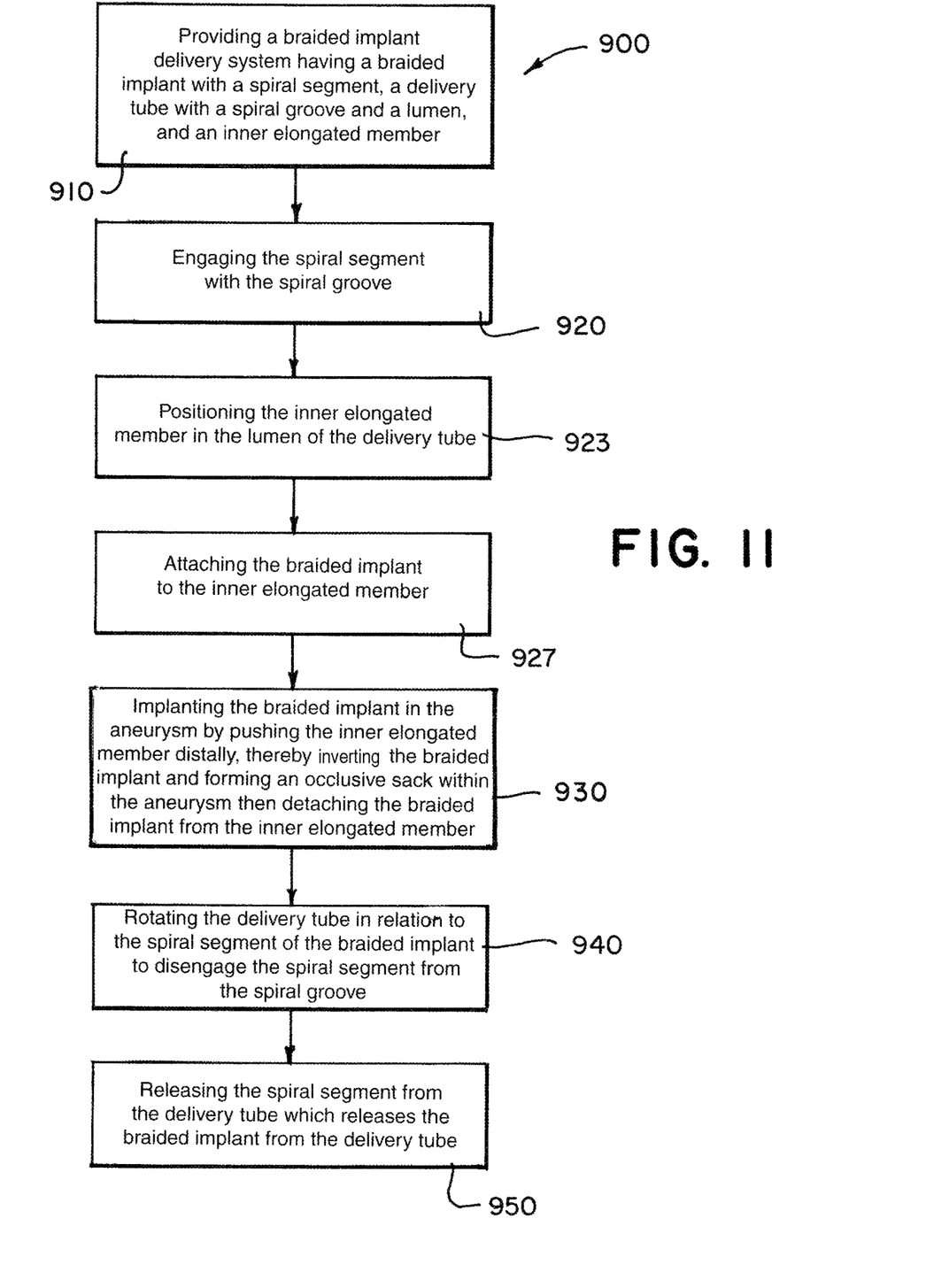

FIGS. 9 to 11 are flow diagrams outlining example method steps for use of a device or system for treating an aneurysm 10. The method steps can be implemented by any of the example means described herein or by any means that would be known to one of ordinary skill in the art.

Referring to method 700 outlined in FIG. 9, in step 710 a braided implant delivery system having a delivery tube and a braided implant can be provided. The braided implant can have a spiral segment and the delivery tube can have a spiral groove. The braided implant delivery system can be any of the delivery systems described herein having any combination of the features described herein, as well as any features that would be known to one skilled in the art. In step 720 the spiral segment of the braided implant can be engaged with the spiral groove of the delivery tube. In step 730 the braided implant can be implanted in the aneurysm. In step 740 the delivery tube can be rotated in relation to the spiral segment to disengage the spiral segment from the spiral groove. In step 750 the spiral segment can be released from the delivery tube thereby releasing the braided implant from the delivery tube.

Referring to method 800 outlined in FIG. 10, in step 810 a braided implant delivery system having a braided implant and a delivery tube can be provided. The braided implant can have a spiral segment and the delivery tube can have a spiral groove. The braided implant delivery system can be any of the delivery systems described herein having any combination of the features described herein, as well as any features that would be known to one skilled in the art. In step 820 the spiral segment of the braided implant can be engaged with the spiral groove of the delivery tube. In step 830 the braided implant can be implanted in the aneurysm by forming an occlusive sack having an opening within the aneurysm. In step 835 the occlusive sack can contact a wall of the aneurysm. In step 840 the delivery tube can be rotated in relation to the spiral segment to disengage the spiral segment from the spiral groove. In step 845 a contact between the aneurysm wall and the occlusive sack can resist a rotation of the occlusive sack in response to the rotation of the delivery tube. In step 850 the spiral segment can be released from the delivery tube thereby releasing the braided implant from the delivery tube. In step 860 a portion of the spiral segment can be moved from a circular helix shape to a conical helix or flat spiral shape. In step 870 at least a portion of the neck of the aneurysm can be occluded by obstructing at least a portion of the opening of the occlusive sack with the spiral segment.

Referring to method 900 outlined in FIG. 11, in step 910 a braided implant delivery system having a braided implant, a delivery tube, and an inner elongated member can be provided. The braided implant can have a spiral segment and the delivery tube can have a spiral groove and a lumen. The braided implant delivery system can be any of the delivery systems described herein having any combination of the features described herein, as well as any features that would be known to one skilled in the art. In step 920 the spiral segment of the braided implant can be engaged with the spiral groove of the delivery tube. In step 923 the inner elongated member can be positioned in the lumen of the delivery tube. In step 927 the braided implant can be attached to the inner elongated member. In step 930 the braided implant can be implanted in the aneurysm by pushing the inner elongated member distally, thereby inverting the braided implant and forming an occlusive sack within the aneurysm then detaching the braided implant from the inner elongated member. In step 940 the delivery tube can be rotated in relation to the spiral segment of the braided implant to disengage the spiral segment from the spiral groove. In step 950 the spiral segment can be released from the delivery tube thereby releasing the braided implant from the delivery tube.

The descriptions contained herein are examples of embodiments of the invention and are not intended to limit the scope of the invention. As described herein, the invention contemplates many variations and modifications of a system, device, or method that can be used to treat an aneurysm with a braided implant. Variations can include but are not limited to alternative geometries of elements and components described herein, utilizing any of numerous materials for each component or element (e.g. radiopaque materials, memory shape metals, etc.), utilizing additional components including components to position the braided implant at a treatment site, extract the braided implant, or eject a portion of the braided implant from the interior of the delivery tube, utilizing additional components to perform functions described herein, or utilizing additional components to perform functions not described herein, for example. These modifications would be apparent to those having ordinary skill in the art to which this invention relates and are intended to be within the scope of the claims which follow.

The invention claimed is:

1. A system comprising:
   a delivery tube configured to travel through vasculature and comprising an outer surface comprising a helical groove thereon; and
   a braided implant comprising a braided spiral segment, the spiral segment being positioned within the helical groove and being configured, upon rotation of the delivery tube in relation to the braided implant, to disengage from the helical groove and thereby disengage the braided implant from the delivery tube,
   wherein the braided implant is movable to an implanted shape comprising a braided sack portion which comprises an opening from which the spiral segment extends, and
   wherein the spiral segment is configured to form a conical helix shape obstructing the opening of the braided sack portion upon disengaging from the helical groove.

2. The system of claim 1, wherein the spiral segment is configured to contract radially upon disengaging from the helical groove.

3. The system of claim 1,
   wherein the spiral segment comprises a memory shape metal, and
   wherein the memory shape metal is configured to move from a deformed shape when the spiral segment is positioned within the helical groove to a predetermined shape upon disengaging from the helical groove.

4. The system of claim 1, wherein the braided implant comprises:
   an outer tubular segment attached to the spiral segment and positioned over a portion of the outer surface of the delivery tube;
   an inner tubular segment positioned within a lumen of the delivery tube; and
   a fold positioned distal a distal end of the delivery tube from which the outer tubular segment and the inner tubular segment extend proximally.

5. The system of claim 4, further comprising an inner elongated member disposed within the lumen of the delivery tube and configured to push the inner tubular segment distally through the lumen of the delivery tube.

6. The system of claim 4, wherein at least a portion of the inner tubular segment is configured to invert when the inner tubular segment is pushed distally out of the lumen of the delivery tube.

7. An implantation system comprising:
   a delivery tube comprising a helical groove thereon; and
   an implant comprising:
   a tubular braid, and
   a braided spiral segment comprising a common weave with the tubular braid,
   wherein the braided spiral segment is positioned within the helical groove and is configured, upon rotation of the delivery tube in relation to the tubular braid, to disengage from the helical groove and thereby disengage the implant from the delivery tube,
   wherein the tubular braid is movable to an implanted shape comprising an opening from which the braided spiral segment extends, and
   wherein the braided spiral segment is configured to form a conical helix shape obstructing the opening of the implanted shape of the tubular braid upon the braided spiral segment disengaging from the helical groove.

8. The implantation system of claim 7, wherein the braided spiral segment is configured to contract radially upon disengaging from the helical groove.

9. The implantation system of claim 7,
   wherein the braided spiral segment comprises a memory shape metal configured to move from a deformed shape when the braided spiral segment is positioned within the helical groove to a predetermined shape upon the braided spiral segment disengaging from the helical groove.

10. The implantation system of claim 7, wherein the tubular braid comprises:
   an outer tubular segment attached to the spiral segment and positioned over an outer surface of the delivery tube;
   an inner tubular segment positioned within a lumen of the delivery tube; and
   a fold positioned distal a distal end of the delivery tube from which the outer tubular segment and the inner tubular segment extend proximally.

11. The implantation system of claim 10, further comprising an inner elongated member disposed within the lumen of the delivery tube and configured to push the inner tubular segment distally through the lumen of the delivery tube.

12. The implantation system of claim 7, wherein at least a portion of the tubular braid is configured to invert when the implant is moved from a delivery configuration to an implanted configuration.

13. A method comprising:
   collapsing a braided end portion of a braided implant within a helical groove on a delivery tube so that the braided end portion is positioned over an outer surface of the delivery tube and releasable from the delivery tube upon rotation of the delivery tube in relation to the braided implant;
   inserting a majority of the braided implant within a lumen of the delivery tube;
   configuring the delivery tube and braided implant for delivery through vasculature;
   moving the braided implant to an implanted shape comprising an opening from which the braided end portion extends; and
   disengaging the braided end portion from the helical groove, thereby causing the braided end portion to contract radially in a conical helix shape within the opening of the implanted shape and to obstruct the opening of the implanted shape.

14. The method of claim 13, further comprising:
shaping the braided end portion such that the braided end portion is contracts radially upon disengaging from the helical groove.

15. The method of claim 13, further comprising:
forming the braided end portion to comprise a memory shape metal configured to move from a deformed shape when the braided end portion is positioned within the helical groove to a predetermined shape upon the braided end portion disengaging from the helical groove.

16. The method of claim 13, further comprising:
pushing the majority of the braided implant distally from the lumen of the delivery tube.

17. The method of claim 16, further comprising:
inverting a tubular portion of the braided implant as the tubular portion is pushed distally from the lumen of the delivery tube.

* * * * *